United States Patent
Hu et al.

(10) Patent No.: US 9,611,272 B2
(45) Date of Patent: Apr. 4, 2017

(54) POLYMORPHIC FORMS OF ICOTINIB AND USES THEREOF

(71) Applicant: BETTA PHARMACEUTICALS CO., LTD, Zhejiang (CN)

(72) Inventors: Shaojing Hu, Beijing (CN); Wei Long, Beijing (CN); Fei Wang, Beijing (CN); Yinxiang Wang, Beijing (CN); Lieming Ding, Zhejiang (CN)

(73) Assignee: BETTA PHARMACEUTICALS CO., LTD., Hangzhou, Zhejiang (CN)

( * ) Notice: Subject to any disclaimer, the term of this patent is extended or adjusted under 35 U.S.C. 154(b) by 0 days.

(21) Appl. No.: 14/896,992

(22) PCT Filed: Jun. 9, 2014

(86) PCT No.: PCT/CN2014/079491
§ 371 (c)(1),
(2) Date: Dec. 9, 2015

(87) PCT Pub. No.: WO2014/198212
PCT Pub. Date: Dec. 18, 2014

(65) Prior Publication Data
US 2016/0108055 A1  Apr. 21, 2016

(30) Foreign Application Priority Data
Jun. 9, 2013 (WO) ................ PCT/CN2013/077095

(51) Int. Cl.
*A61K 31/519* (2006.01)
*A61K 45/06* (2006.01)
*C07D 491/056* (2006.01)
*A61K 9/20* (2006.01)
*A61K 9/48* (2006.01)

(52) U.S. Cl.
CPC ............ *C07D 491/056* (2013.01); *A61K 9/20* (2013.01); *A61K 9/48* (2013.01); *A61K 31/519* (2013.01); *A61K 45/06* (2013.01)

(58) Field of Classification Search
CPC .. C07D 491/056; A61K 31/519; A61K 45/06; A61K 9/20; A61K 9/48
See application file for complete search history.

(56) References Cited

FOREIGN PATENT DOCUMENTS

| WO | 03082830 A1 | 10/2003 | |
|---|---|---|---|
| WO | WO 03/082830 A1 * | 10/2003 | ........... C07D 239/86 |
| WO | 2010003313 A1 | 1/2010 | |
| WO | 2013064128 A1 | 5/2013 | |

OTHER PUBLICATIONS

International Search Report Issued in International PCT Application PCT/CN2014/079491 dated Sep. 1, 2014.
Hu, Shaojing et al. "Synthesis and biological evaluation of crown ether fused quinazoline analogues as potent EGFR Inhibitors" Bioorganic & Medicinal Chemistry Letters, No. vol. 22, Jun. 28, 2012 (Jun. 28, 2012), pp. 6301-6305 table 1, scheme 1, scheme 2.

* cited by examiner

*Primary Examiner* — Erich A Leeser
(74) *Attorney, Agent, or Firm* — Andrews Kurth Kenyon LLP; David Bradin (57) ABSTRACT

The present invention relates to the polymorphic forms of the compound of Formula I, preparation thereof and pharmaceutical compositions, and use of a polymorph above in the treatment of a disease, a disorder or a condition, or in the manufacturing of a medicament for the treatment of a disease, a disorder or a condition.

Formula I

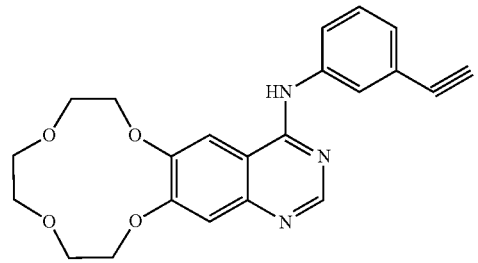

20 Claims, 5 Drawing Sheets

POLYMORPHIC FORMS OF ICOTINIB AND USES THEREOF

This application is a national stage application under 35 U.S.C. §371 based on PCT Application No. PCT/CN2014/079491, entitled "Polymorphic Forms Of Icotinib And Uses Thereof" and filed Jun. 9, 2014, which claims the benefit under 35 U.S.C. 119 (a) of PCT/CN2013/077095, entitled "Polymorphic Forms Of Icotinib And Uses Thereof" and filed Jun. 9, 2013. The entirety of these aforementioned applications is incorporated herein by reference for all purposes.

FIELD OF THE INVENTION

The present invention relates to the polymorphic forms of Icotinib, processes for preparing these polymorphic forms, pharmaceutical compositions thereof, and use of new polymorphic forms and pharmaceutical compositions for the treatment of cancer and cancer occurrence-related diseases.

BACKGROUND OF THE INVENTION

Tyrosine kinase receptors are trans-membrane proteins that, in response to an extracellular stimulus, propagate a signaling cascade to control cell proliferation, angiogenesis, apoptosis and other important features of cell growth. One class of such receptors, epidermal growth factor receptor (EGFR) tyrosine kinases, are overly expressed in many human cancers, including brain, lung, liver, bladder, breast, head and neck, esophagus, gastrointestinal, ovary, cervix or thyroid cancer.

EGFR is expressed in many types of tumor cells. Binding of cognate ligands (including EGF, TGFα (i.e., Transforming Growth Factor-α) and neuregulins) to the extracellular domain causes homo- or heterodimerization between family members. The juxtaposition of cytoplasmic tyrosine kinase domains results in transphosphorylation of specific tyrosine, serine and threonine residues within each cytoplasmic domain. The formed phosphotyrosines act as docking sites for various adaptor molecules and subsequent activation of signal transduction cascades (Ras/mitogen-activated, PI3K/Akt and Jak/STAT) that trigger proliferative cellular responses.

Various molecular and cellular biology and clinical studies have demonstrated that EGFR tyrosine kinase inhibitors can block cancer cell proliferation, metastasis and other EGFR-related signal transduction responses to achieve clinical anti-tumor therapeutic effects. Two oral EGFR kinase inhibitors with similar chemical structures are Gefitinib (Iressa, AstraZeneca), approved by the U.S. FDA for advanced non-small cell lung cancer in 2003 (and later withdrawn), and Erlotinib Hydrochloride (Tarceva, Roche and OSI), approved by the U.S. FDA for advanced non-small cell lung cancer and pancreatic cancer treatment in 2004.

Many pharmaceutically active organic compounds can crystallize in more than one type of three-dimensional crystal structure. That is, the compounds may crystallize in different crystalline forms. This phenomenon (identical chemical structure but different crystalline structure) is referred to as polymorphism, and the species having different molecular structures are referred to as polymorphs.

Polymorphs of a particular organic pharmaceutical compound may have different physical properties, such as solubility and hygroscopicity, due to their distinct three-dimensional crystal structures. However, it is generally not possible to predict whether a particular organic compound will form different crystalline forms, let alone predict the structure and properties of the crystalline forms themselves. The discovery of a new crystalline or polymorph form of a pharmaceutically useful compound may provide a new opportunity for improving the overall characteristics of a pharmaceutical product. It enlarges the repertoire of materials that a formulation scientist has available for designing. It may be advantageous when this repertoire is enlarged by the discovery of new polymorphs of a useful compound.

Chinese Patent Publication No. CN1305860C discloses the structure of Icotinib(free base) on page 29, Example 15, Compound 23, and WO 2010/003313 disclosed Icotinib hydrochloride and its new crystalline polymorphs.

DESCRIPTION OF THE INVENTION

The present invention relates to Icotinib (i.e., the compound of Formula I), approximately pure polymorph forms, and pharmaceutical acceptable salt thereof.

Formula I

The compound of Formula I of the present invention exists in one or more polymorphic forms. These polymorphic forms are referred as Form I, Form II, Form III and Form IV. The compound of Formula I and its polymorphic forms have better solubility and chemical stability, making them preferable for clinical applications.

In one aspect, the polymorph form is of Polymorph Form I and its X-ray powder diffraction pattern having characteristic peaks at diffraction angles 2θ of approximately 7.6°, 14.7°, 20.9°, 23.1° and 27.5°±0.2°.

In some other embodiments of Polymorph Form I, its X-ray powder diffraction pattern has characteristic peaks, expressed in terms of the interplanar distance, of 11.6Å, 6.0Å, 4.3Å, 3.9Å and 3.3Å.

In some embodiments of Polymorph Form I, its X-ray powder diffraction pattern has characteristic peaks at diffraction angles 2θ of approximately 7.6°, 14.7°, 20.9°, 23.1°, 24.2°, 27.5°, 29.8° and 30.9°±0.2°.

In still some other embodiments of Polymorph Form I, its X-ray powder diffraction pattern has characteristic peaks, expressed in terms of the interplanar distance, of 11.6Å, 6.0Å, 4.3Å, 3.9Å, 3.7Å, 3.3Å, 3.0Å and 2.9Å.

Figure 1:
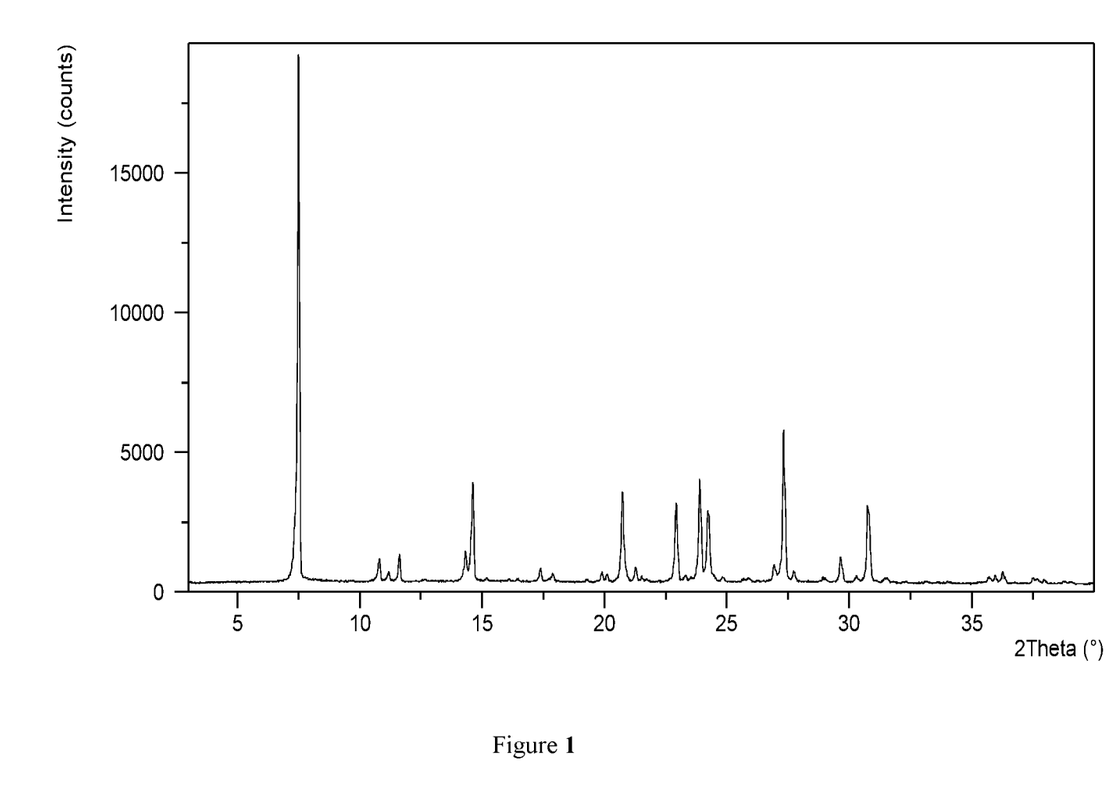
FIG. 1: The X-ray powder diffraction pattern of Polymorph Form I of compound of Formula I.

Preferably, the X-ray powder diffraction pattern is shown as in FIG. 1.

Preferably, the melting point of the Polymorph Form I is 175-177° C.

The present also provides a method of preparing the polymorph, comprising the steps of dissolving Icotinib hydrochloride in the mixture of $C_1$-$C_4$ alcohol and water, the mixture was warmed to 60° C. and a solution of base was dropped. The reaction solution was stirred for 1 h and cooled down to room temperature. The precipitate was filtered and washed with purified water and dried 8 h in vacuum below 60° C. to obtain the resulted Polymorph Form I.

In another aspect, the polymorph form is of Polymorph Form II and its X-ray powder diffraction pattern has characteristic peaks at diffraction angles 2θ of approximately 5.5°, 19.7° and 22.6°±0.2°.

In still some other embodiments of Polymorph Form II, its X-ray powder diffraction pattern has characteristic peaks, expressed in terms of the interplanar distance, of 16.0Å, 4.5Å and 3.9Å.

In some embodiments of Polymorph Form II, its X-ray powder diffraction pattern has characteristic peaks at diffraction angles 2θ of approximately 5.5°, 11.0°, 19.7°, 20.9° and 22.6°±0.2°.

In still some other embodiments of Polymorph Form II, its X-ray powder diffraction pattern has characteristic peaks, expressed in terms of the interplanar distance, of 16.0Å, 8.0Å, 4.5Å, 4.3Å, and 3.9Å.

In some other embodiments of Polymorph Form II, its X-ray powder diffraction pattern has characteristic peaks at diffraction angles 2θ of approximately 5.5°, 8.8°, 11.0°, 16.5°, 19.7°, 20.9°, 22.6° and 23.7°±0.2°.

In still some other embodiments of Polymorph Form II, its X-ray powder diffraction pattern has characteristic peaks, expressed in terms of the interplanar distance of 16.0Å, 10.1Å, 8.0Å, 5.4Å, 4.5Å, 4.3Å, 3.9Å and 3.8Å.

Figure 2:
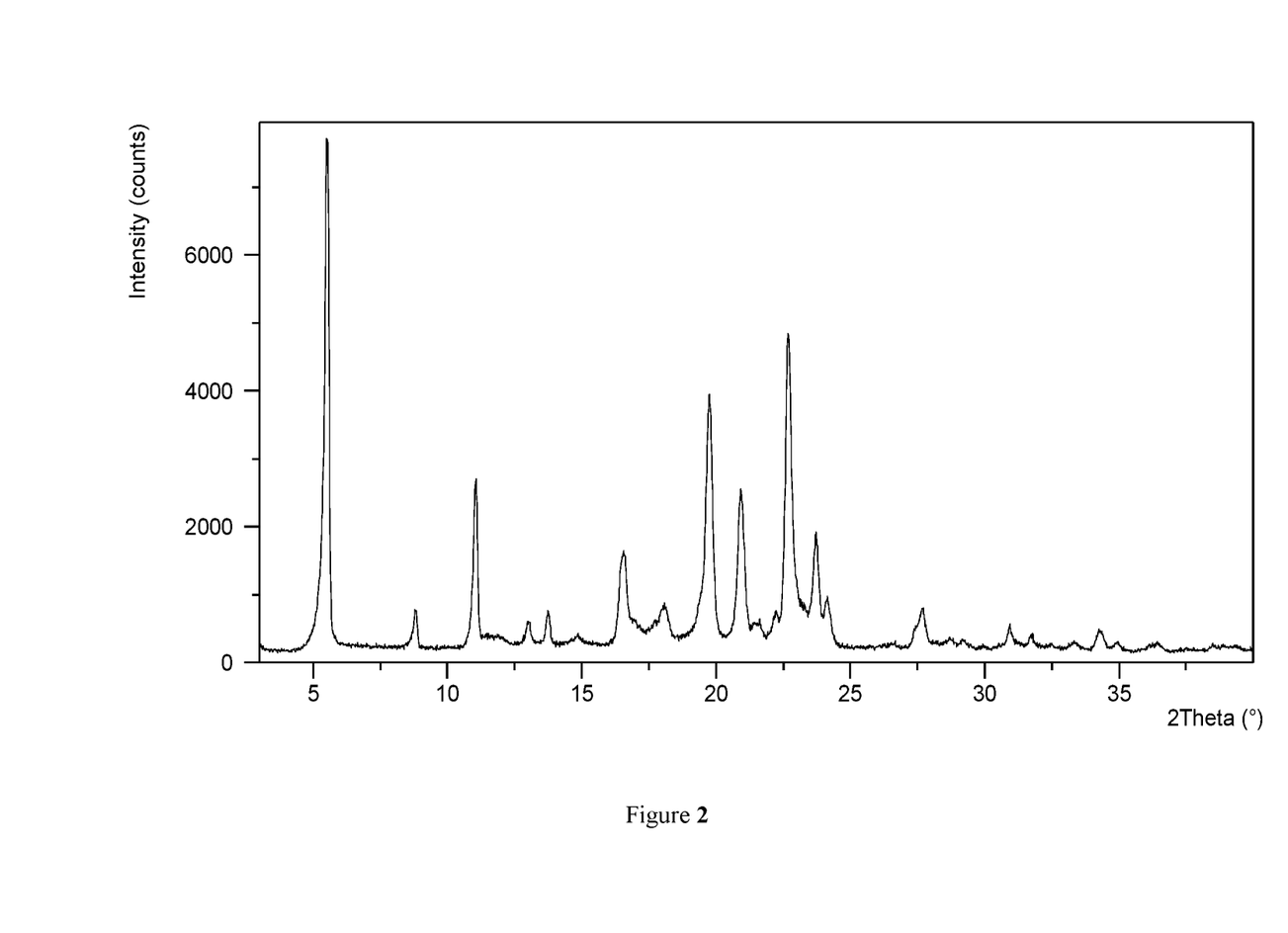
FIG. 2: The X-ray powder diffraction pattern of Polymorph Form II of compound of Formula I.

Preferably, the X-ray powder diffraction pattern is shown as in FIG. 2.

Preferably, the melting point of the Polymorph Form II is 176-178° C.

The present invention also provides a method of preparing the polymorph comprising the steps of heating the polymorph of Form I to about 165° C. under $N_2$, and cooling down to room temperature naturally to recover the resulted Polymorph Form II.

In another aspect, the polymorph form is of Polymorph Form III and its X-ray powder diffraction pattern has characteristic peaks at diffraction angles 2θ of approximately 5.1°, 16.7°, 20.9°, 21.7° and 23.9°±0.2°.

In some other embodiments of Polymorph Form III, its X-ray powder diffraction pattern has characteristic peaks, expressed in terms of the interplanar distance, of 17.3Å, 5.3Å, 4.3Å, 4.1Å and 3.7Å.

In some embodiments of Polymorph Form III, its X-ray powder diffraction pattern has characteristic peaks at diffraction angles 2θ of approximately 5.1°, 7.6°, 16.7°, 19.8°, 20.9°, 21.7°, 23.9° and 24.7°±0.2°.

In still some other embodiments of Polymorph Form III, its X-ray powder diffraction pattern has characteristic peaks, expressed in terms of the interplanar distance, of 17.3Å, 11.7Å, 5.3Å, 4.5Å, 4.3Å, 4.1Å, 3.7Å and 3.6 Å.

Figure 3:
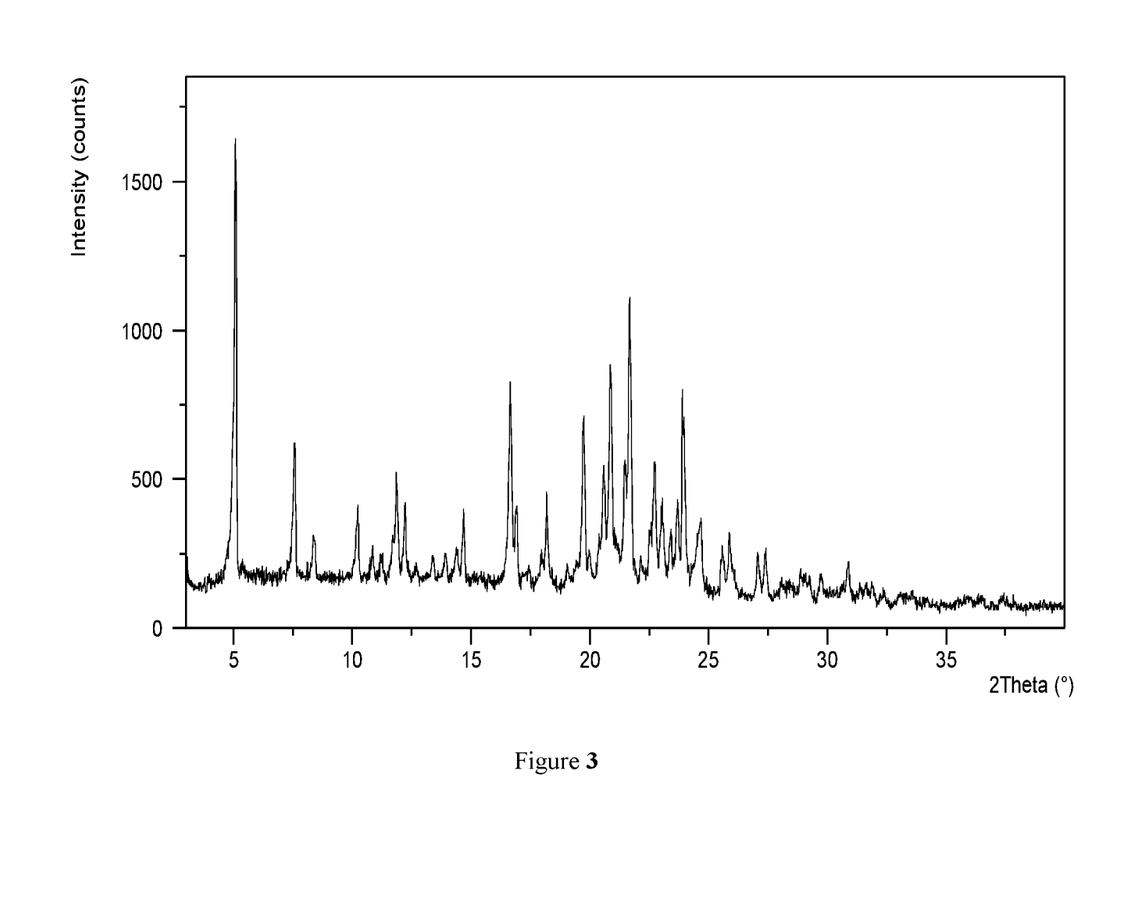
FIG. 3: The X-ray powder diffraction pattern of Polymorph Form III of compound of Formula I.

Preferably, the X-ray powder diffraction pattern is shown as in FIG. 3.

Preferably, the melting point of the Polymorph Form III is 175-178° C.

The present also provides a method of preparing the polymorph, comprising the steps of putting the polymorph of Form I in the saturated vapor of acetonitrile at room temperature for a week, and recovering the resulted Polymorph Form III.

In another aspect, the polymorph form is of Polymorph Form IV and its X-ray powder diffraction pattern has characteristic peaks at diffraction angles 2θ of approximately 6.1°, 11.2°, 15.8°, 19.5° and 22.5°±0.2°.

In some other embodiments of Polymorph Form IV, its X-ray powder diffraction pattern has characteristic peaks, expressed in terms of the interplanar distance, of 14.5Å, 7.9Å, 5.6Å, 4.6Å and 4.0Å.

In some embodiments of Polymorph Form IV, its X-ray powder diffraction pattern has characteristic peaks at diffraction angles 2θ of approximately 6.1°, 11.2°, 12.9°, 14.2°, 15.8°, 18.3°, 19.5° and 22.5°±0.2°.

In still some other embodiments of Polymorph Form IV, its X-ray powder diffraction pattern has characteristic peaks, expressed in terms of the interplanar distance, of 14.5Å, 7.9Å, 6.9Å, 6.2Å, 5.6Å, 4.9Å, 4.6Å and 4.0Å.

Figure 4:
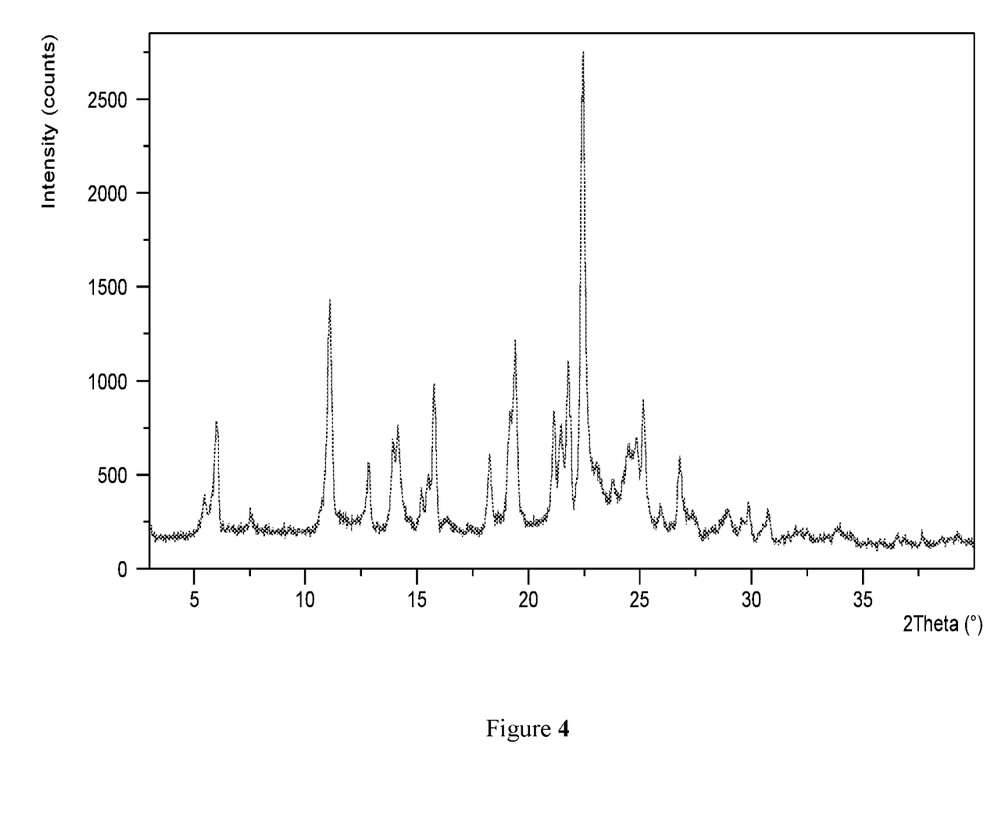
FIG. 4: The X-ray powder diffraction pattern of Polymorph Form IV of compound of Formula I.

Preferably, the X-ray powder diffraction pattern is shown as in FIG. 4.

Preferably, the melting point of the Polymorph Form IV is 175-177° C.

The present invention also provides a method of preparing the polymorph comprising the steps of putting the polymorph of Form I in the saturated vapor of methanol at room temperature for a week, and recovering the resulted Polymorph Form IV.

Polymorph Form I, II, III or IV of this invention can have a purity of ≥85%, ≥95%, or even ≥99%.

In still another aspect, the invention provides processes for preparing a polymorph form of Icotinib, comprising the step of reacting Icotinib hydrochloride with a base in a media to produce Icotinib in the polymorph form. This reaction can be carried out, for example, at the temperature of 40-80° C.

Examples of a suitable base include sodium hydroxide, potassium hydroxide, sodium carbonate, and potassium carbonate.

The second reaction media can include, e.g., water and ethanol, water and isopropanol, water and methanol, or water and tetrahydrofuran.

The polymorph forms of this invention, particularly Polymorph Form I, Polymorph Form II, Polymorph Form III and Polymorph Form IV, unexpected exhibited significantly better bioavailability and chemical stability than Icotinib hydrochloride, the active ingredient of a drug currently in the marketplace. Accordingly, the invention further provides pharmaceutical compositions comprising a therapeutically effective amount of a polymorph form of this invention and a pharmaceutically acceptable excipient, adjuvant or carrier.

The pharmaceutical composition can further include a second therapeutically active ingredient, and can be in a form suitable for oral administration (e.g., a tablet or capsule).

Also within the scope of this invention is the use of a polymorph form or a pharmaceutical composition of this invention in the manufacturing of a medicament for the prevention or treatment in mammals of an excessive non-malignant disease, pancreatitis, kidney disease, cancer, angiogenesis or vascular disease, or for mammalian embryo cell transplantation.

The excessive non-malignant disease can be, for example, benign skin hyperplasia or benign prostatic hyperplasia. Or, the excessive non-malignant disease, pancreatitis, kidney disease, cancer, angiogenesis or vascular occurrence-related illness is selected from: tumor angiogensis, chronic inflammatory disease such as rheumatoid arthritis, atherosclerosis atherosclerosis, skin diseases such as psoriasis, and scleroderma, diabetes-induced skin diseases, diabetic retinopathy, premature retinopathy, age related degeneration stains, hemangionma, glioma, Kaposiinternal tumor, ovarian cancer, breast cancer, hung cancer, pancreatic cancer, lymphoma, prostate, colon and skin tumors and their complications.

All the polymorphs of the present invention are approximately pure.

The term "approximately pure" as herein used refers to at least 85 wt %, preferably at least 95 wt %, more preferably at least 99 wt % of the compound of Formula I exists in a polymorphic form of the present invention, particularly in the polymorphic forms of Form I, Form II, Form III or Form IV.

The main peaks described in the polymorphs above are reproducible and are within the error limit (the specified value ±0.2).

In the present invention, "the X-ray powder diffraction pattern is shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 2, 3 or 4 refers to the X-ray powder diffraction pattern that show major peaks as in FIG. 2, 3 or 4 wherein major peaks refer to those with the relative intensity greater than 10%, preferably greater than 30%, relative to the highest peak (with its relative intensity designated to be 100%) in FIG. 2, 3 or 4 respectively.

Crystallization in the present invention is related to dynamics and equilibria among different polymorphic forms under certain conditions. Therefore, those skilled in the art will realize that the resulting polymorphic form depends on the kinetics and thermodynamics of the crystallization process. Under certain conditions (solvent system, temperature, pressure, and the concentration of the compound of the present invention), a polymorphic form may be more stable than another one (or, actually be more stable than any other polymorphic forms). However, the polymorphs that are less stable thermodynamically may be favorable in kinetics. The polymorph form may also be affected by factors other than kinetics, such as time, impurity distribution, agitation, presence or absence of polymorphic seed. For purposes of this invention, various hydrate and solvate forms are included in the scope of "polymorph".

The present invention further provides a pharmaceutical composition, comprising a therapeutically effective amount of one or more polymorphs of Form I, Form II, Form III, or Form IV of the compound of Formula I, and a pharmaceutically acceptable excipient, adjuvant or carrier. Wherein, the pharmaceutical composition contains 0.01 wt %-99 wt %, preferably 1 wt %-70 wt %, more preferably 10 wt %-50 wt % of any one polymorph of Form I, Form II, Form III, or Form IV of the compound of Formula I.

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound of the present invention can be administrated via oral, inhalation, rectal, parenteral or topical administration to a subject who needs treatment. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition of the present invention can be produced by the conventional methods in the pharmaceutical field. For example, the active ingredient can be mixed with one or more excipients, then to make the desired formulation. The "pharmaceutically acceptable carrier" refers to conventional pharmaceutical carriers suitable for the desired pharmaceutical formulation, for example: a diluent, a vehicle such as water, various organic solvents, etc, a filler such as starch, sucrose, etc; a binder such as cellulose derivatives, alginates, gelatin and polyvinylpyrrolidone (PVP); a wetting agent such as glycerol;

a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye. Preferably, the excipient is suitable for desired formulation and administration type.

The term "disease" or "disorder" or "condition" refers to any disease, discomfort, illness, symptoms or indications.

In another aspect, the present invention provides use of the compounds (Icotinib and its polymorphs) and/or the pharmaceutical compositions in manufacturing a medicament for the treatment or prevention in mammals of excessive non-malignant hyperplasia disease, pancreatitis, kidney disease, cancer, angiogenesis or vascular occurrence-related illness, or for the mammalian embryo cell transplantation. The excessive non-malignant hyperplasia disease can be a benign skin hyperplasia or a benign prostatic hyperplasia.

Preferably, the polymorphs or pharmaceutical composition of the present invention can be used in manufacturing a medicament for the treatment or prevention in mammals of excessive non-malignant hyperplasia disease, pancreatitis, kidney disease, cancer, angiogenesis or vascular occurrence-related illness selected from tumor angiogenesis, chronic inflammatory diseases such as rheumatoid arthritis, atherosclerosis, skin diseases such as psoriasis, and scleroderma, diabetes included skin diseases, diabetic retinopathy, premature retinopathy, age-related degeneration stains, hemangioma, glioma, Kaposi internal tumor, ovarian cancer, breast cancer, lung cancer, pancreatic cancer, lymphoma, prostate, colon and skin tumors and their complications.

Among the mammals mentioned herein, human beings are preferred.

This invention provides a method for treating malignant tissue hyperplasia in mammals. This treatment method includes application of an effective amount of Icotinib and/or its polymorph forms and/or the pharmaceutical compositions to mammalian patients with hyperplasia disease. In some embodiments, the treatment method also includes use of MMP (matrix metalloproteinase) inhibitor, VEGFR (vascular endothelial growth factor receptor) kinase inhibitors, HER2 inhibitor, VEGFR antibody drugs, and/or endostatin drugs. In some embodiments, the treatment method also includes using one or more anti-tumor agents such as mitotic inhibitors, alkylating agents, anti-metabolites, tumor antibiotics, growth factor inhibitors, cell cycle inhibitors, enzymes, enzyme inhibitors, biological response modifiers, anti-hormone drugs and so on. The anti-tumor agents can be selected from carboplatin, paclitaxel, gemcitabine, methotrexate, 5-FU, camptothecin, cyclophosphamide, BCNU and other medications.

Another purpose of this invention is to provide the use of the compounds (Icotinib and its polymorphs) and/or the pharmaceutical compositions in manufacturing a medicament for treating a disease related to tyrosine kinase dysfunction.

Preferably, this invention provides a method for the treatment of disease caused by tyrosine kinase dysfunction. This treatment method includes administering to a patient with the disease caused by tyrosine kinase dysfunction an effective amount of the compounds (Icotinib and its polymorphs) and/or the pharmaceutical compositions. The tyrosine kinase dysfunction-related disease include, but are not limited to disease of brain, lung, liver, bladder, breast, head and neck, esophagus, gastrointestinal tract, ovary, cervix or thyroid tumors and their complications.

Target disease for the just described treatment method are preferably selected from brain cancer, lung cancer (such as non-small cell lung cancer (NSCLC)), kidney cancer, bone cancer, liver cancer, bladder cancer, chest cancer, lymphoma, or thyroid tumors and their complications.

The above-described methods can be applied in combination with any chemical therapy, biological therapy or radiation therapy.

The above-described treatment methods can further include application of anti-EGFR antibodies, anti-EGF antibodies, or both, in the same treatment.

The dosage of the active ingredient or compound when administered will be determined by the individual needs of the patient to treated, administration route, severity of disease or illness, dosing schedule, as well as evaluation and judgment of the designated doctor. However, based on the active compound, the preferred range of the effective dosage can be approximately 0.01-120 mg daily per kilogram of body weight; or more preferably 1-50 mg per day per kilogram of body weight in single or separate doses. In some cases, it is more suitable to apply the lower end of the above-described dosage range, while in other cases the higher dosage may be used without causing harmful side effects.

Another aspect of the present invention is to provide Icotinib for clinical applications. In particular, the present invention related to clinical treatment with Icotinib with the following treatment options for cancer patients: the dosage of Icotinib and/or polymorph Form I, II, III, or IV can be 25-2100 mg/day with the administration frequency being 1-3 times a day; a preferred dosage is 75-1200 mg/day with the administration frequency being 2-3 times a day; an even more preferred dosage is 100-1200 mg/day with the administration frequency being 2-3 times a day.

EXAMPLES

The present invention is further exemplified, but not limited, by the following examples that illustrate the invention. The techniques or methods used in these examples, unless expressly stated otherwise, were conventional techniques or methods well known in the art.

The X-ray powder diffraction (XRPD) patterns for the crystalline forms of Icotinib were generated on a PANalytical X-ray Diffraction System with Empyrean console. The diffraction peak positions were calibrated using silicon powder which had a 2θ value of 28.443 degree. An Empyrean Cu LEF X-ray tube K-Alpha radiation was used as the source.

Example 1

Preparation of Form I 100 g Icotinib hydrochloride was dissolved in the mixture of 300 ml ethanol and 200 ml water. A solution of 11.2 g sodium hydroxide in 100 ml water was added dropwisely at 60° C. to the Icotinib hydrochloride solution until the pH value of the reaction solution reached 13. The reaction solution was then stirred for an hour and then cooled down to the room temperature. The precipitate was filtered and washed with purified water and dried for 8 hours under vacuum below 60° C. to obtain 90 g the desired Form I. And the melting point of the Polymorph Form I is 175-177° C.

Example 2

Preparation of Form I 10 g Icotinib hydrochloride was first dissolved in the mixture of 30 ml isopropanol and 20 ml water, a solution of 1.6 g potassium hydroxide in 10 ml water was added to the Icotinib hydrochloride solution until the pH value of the reaction mixture reached 13. The reaction solution was then stirred for 1-2 hrs and cooling down to the room temperature. The precipitate was filtered and washed with purified water and dried under vacuum for 8-10 hours at a temperature below 50° C. to give 7.9 g the desired Form I.

Example 3

Preparation of Form I 5 g Icotinib hydrochloride was dissolved in the mixture of 20 ml methanol and 15 ml water. To this Icotinib hydrochloride solution was then added dropwisely a solution of 1.5 g sodium carbonate in 10 ml water at 40° C. until the pH value of the resultant mixture reached 13. The reaction solution was then stirred for 1-2 hrs before cooling down to the room temperature. The precipitate was filtered and washed with purified water and then dried under vacuum for 8-10 hrs below 60° C. to obtain 4 g the desired Form I.

Example 4

Preparation of Form I 5 g Icotinib hydrochloride was dissolved in a mixture of 20 ml tetrahydrofuran and 15 ml water, and then to this Icotinib solution was added a solution of 1.9 g potassium carbonate in 10 ml water dropped at 50° C. until the pH value of resultant reaction mixture reached 13. The reaction solution was then stirred for 1-2 hrs before cooling down to the room temperature to give a precipitate. The precipitate was filtered and washed with purified water and then dried for 8-10 hrs under vacuum at a temperature below 60° C. to give 4 g the desired Form I.

Example 5

Preparation of Form II

Form I prepared from the method of Example 1 was heated to 150° C. under $N_2$, then cooled down to room temperature naturally to obtain the desired Form II. And the melting point of the Polymorph Form is II 176-178° C.

Example 6

Preparation of Form II

Form I prepared from the method of Example 1 was heated to 160° C. under $N_2$, then cooled down to room temperature naturally to obtain the desired Form II.

Example 7

Preparation of Form II

Form I prepared from the method of Example 1 was heated to 170° C. under $N_2$, then cooled down to room temperature naturally to obtain the desired Form II.

Example 8

Preparation of Form II

Form I prepared from the method of Example 1 was heated to 180° C. under N₂, then cooled down to room temperature naturally to obtain the desired Form II.

Example 9

Preparation of Form II

Form I prepared from the method of Example 1 was heated to 165° C. under N₂, then cooled down to room temperature naturally to obtain the desired Form II.

Example 10

Preparation of Form III 15 mg Form I prepared from the method of Example 1 was put into a 3-ml vial. This vial was placed inside a 20 ml vial filled with saturated vapor of acetonitrile. The large vial was sealed and kept at room temperature for one week, recovered the desired polymorph. And the melting point of the Polymorph Form III is 175-178° C.

Example 11

Preparation of Form IV 15 mg Form I prepared from the method of Example 1 was put into a 3-ml vial. This vial was placed inside a 20 ml vial filled with saturated vapor of methanol. The larger vial was sealed and kept at room temperature for one week, and recovered the desired polymorph. And the melting point of the Polymorph Form is IV 175-177° C.

Example 12

Pharmacokinetic Study of Icotinib Hydrochloride and the Polymorph Form II of Icotinib Drugs and reagents: the Icotinib hydrochloride used in this study was of Crystalline Form I disclosed by the WO2010/003313. Polymorph Form II of Icotinib and Icotinib hydrochloride were ground to fine particles. The material content (purity) was not less than 99.0%. Sodium carboxymethyl cellulose was medical supply graded.

Experimental animals: SD rats were divided to the Icotinib hydrochloride group and a Polymorph Form II group.

Pharmaceutical preparation: the amount of each compound was weighed and then sodium carboxymethyl cellulose was added to result in the test compound's concentration of 0.5%. The solid mixture was then added to prepare a suspension thereof at a final concentration of 10 mg/ml in water.

Administration and sample collection: each suspension was administered orally to fasted SD rats at a dose equivalent to 50 mg/kg Icotinib in a dose volume of 5 ml/kg. 0.4 ml of blood was collected in EDTA-K pre anticoagulant tubes at time intervals of 0.5, 1, 1.5, 2, 4, 6, 8 and 24 hours after the administration of the test compound, centrifuged at 3000 rpm for 10 minutes, and 120 μl plasma was collected and kept in cold storage.

Figure 5:
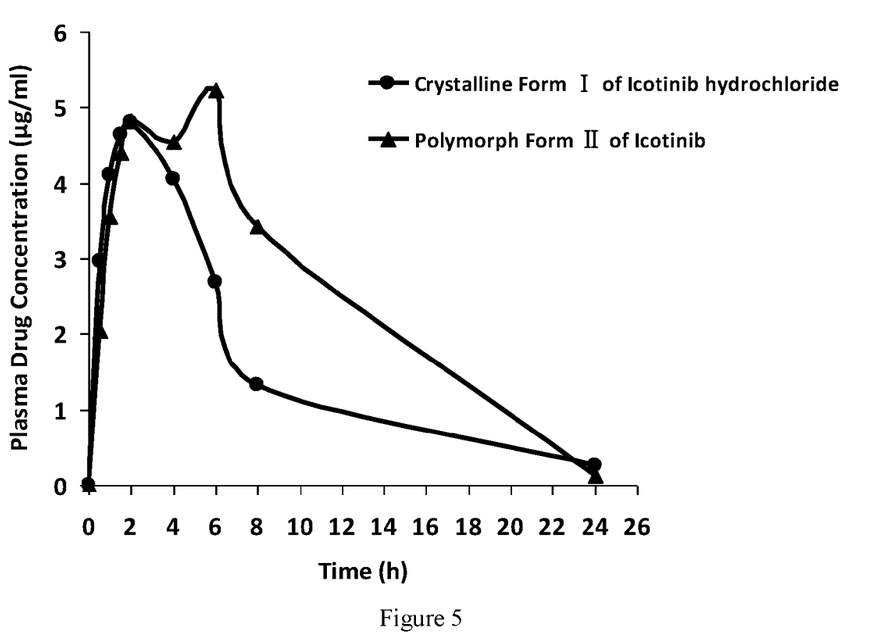
FIG. 5: The plasma concentration-time curves of Crystalline Form I Icotinib hydrochloride and Polymorph Form II of the compound of Formula I.

Samples were analyzed by high performance liquid chromatography. The chromatographic conditions utilized C18-silane bonded silica as stationary phase, 0.02 mol/L of sodium dihydrogen phosphate in acetonitrile (40:60, using sodium hydroxide solution to adjust pH to 5.0) as the mobile phase and a detection wavelength of 334 nm. PK profile comparison of Polymorph Form II of Icotinib and Crystalline Form I of Icotinib hydrochloride was summarized in Table 1 and FIG. 5. Polymorph Form II of Icotinib showed higher bioavailability than Crystalline Form I of Icotinib hydrochloride.

TABLE 1

| Group | Gender | $AUC_{(0-24)}$ (mg/L * h) | $AUC_{(0-\infty)}$ (mg/L * h) | $T_{1/2}$ (h) | $T_{max}$ (h) | $C_{max}$ (mg/L) |
|---|---|---|---|---|---|---|
| Crystalline Form I of Icotinib hydrochloride | Male | 39.2 ± 27.6 | 39.8 ± 28.5 | 3.1 ± 1.4 | 1.3 ± 1.1 | 4.9 ± 2.6 |
| Polymorph Form II of Icotinib | Male | 62.4 ± 30.1 | 63.0 ± 30.0 | 3.5 ± 0.6 | 4.5 ± 2.6 | 5.8 ± 2.6 |

Example 13

Formulation of a Hard Gel Capsule

As a specific embodiment of an oral composition, about 100 mg of the Polymorph Form of Example 1-11 is formulated with sufficient finely divided lactose to provide a total amount of about 580 mg to about 590 mg to fill a size 0 hard gel capsule.

Although the present invention has been fully described in connection with embodiments thereof with reference to the accompanying drawings, it is to be noted that various change and modifications will become apparent to those skilled in the art. Such changes and modifications are to be understood as being included within the scope of the present invention as defined by the appended Claims.

What is claimed is:
1. A polymorph form of the compound of Formula I,

Formula I wherein the polymorph form is of Form II and its X-ray powder diffraction pattern has characteristic peaks at diffraction angles 2θ of 5.5°, 11.0°, 19.7°, 20.9° and 22.6°±0.2°.

2. The polymorph form of claim 1, wherein its X-ray powder diffraction pattern has characteristic peaks at diffraction angles 2θ of 5.5°, 8.8°, 11.0°, 16.5°, 19.7°, 20.9°, 22.6° and 23.7°±0.2°.

3. The polymorph form of claim 1, wherein the X-ray powder diffraction pattern is shown as in FIG. 2.

4. The polymorph form of claim 1, wherein the melting point is 176-178° C.

5. A method of preparing a polymorph form of claim 1, comprising:
a) dissolving Icotinib hydrochloride in the mixture of ethanol and water, warming the mixture to 40-60° C. and dropping a solution of base; then stirring the solution for 1 hr, cooling the mixture down to room temperature and recovering a polymorph form; and
b) heating the polymorph form of step a) to a temperature of 150-180° C. under $N_2$, then naturally cooling the polymorph down to room temperature to obtain the resulting polymorph form.

6. The method of claim 5, wherein the temperature of b) is 160-170° C.

7. The method of claim 6, wherein the temperature is 165° C.

8. A pharmaceutical composition comprising a therapeutically effective amount of the polymorph of claim 1, and a pharmaceutically acceptable excipient, adjuvant or carrier.

9. The pharmaceutical composition of claim 8, wherein the polymorph form of claim 1 has a purity of ≥85 wt %.

10. The pharmaceutical composition of claim 8, wherein the polymorph form of claim 1 has a purity of ≥99 wt %.

11. The pharmaceutical composition of claim 8, further comprising a second therapeutically active ingredient.

12. The pharmaceutical composition of claim 8, wherein the pharmaceutical composition is suitable for oral administration.

13. The pharmaceutical composition of claim 8, wherein the pharmaceutical composition is in the form of tablet or capsule.

14. The pharmaceutical composition of claim 8, wherein the composition comprises 0.01 wt %-99 wt % of the polymorph form of claim 1.

15. The pharmaceutical composition of claim 14, wherein the composition comprises 10 wt %-50 wt % of the polymorph form of claim 1.

16. A method for treating a disease related to tyrosine kinase dysfunction, comprising administering to a patient with the disease with a therapeutically effective amount of the Form of claim 1.

17. The method of claim 16, further comprising administering to the patient a matrix metalloproteinase inhibitor, a vascular endothelial growth factor receptor kinase inhibitor, an HER 2 inhibitor, a vascular endothelial growth factor receptor antibody drug, or an endostatin drug.

18. The method of claim 16, further comprising administering to the patient an anti-tumor agent selected from: mitotic inhibitors, alkylating agents, anti-metabolites, tumor antibiotics, growth factor inhibitors, cell cycle inhibitors, enzymes, enzyme inhibitors, biological response modifiers, and anti-hormones drugs.

19. A method for treating a disease related to tyrosine kinase dysfunction, comprising administering to a patient with the disease with a therapeutic effective amount of the compound of the polymorph form of claim 1.

20. The method of claim 19, wherein the diseases is brain cancer, lung cancer, kidney cancer, bone cancer, liver cancer, bladder cancer, head and neck cancer, esophageal cancer, stomach, colon, rectum cancer, breast cancer, ovarian cancer, melanoma, skin cancer, adrenal cancer, cervical cancer, lymphoma, or thyroid tumors and their complications.

* * * * *